(12) United States Patent
Marfurt (10) Patent No.: US 7,964,372 B2
(45) Date of Patent: Jun. 21, 2011

(54) SIZE SELF-LIMITING COMPOSITIONS AND TEST DEVICES FOR MEASURING ANALYTES IN BIOLOGICAL FLUIDS

(75) Inventor: Karen L. Marfurt, Edwardsburg, MI (US)

(73) Assignee: Bayer HealthCare LLC, Tarrytown, NY (US)

(*) Notice: Subject to any disclaimer, the term of this patent is extended or adjusted under 35 U.S.C. 154(b) by 707 days.

(21) Appl. No.: 11/792,456

(22) PCT Filed: Dec. 12, 2005

(86) PCT No.: PCT/US2005/045235
§ 371 (c)(1),
(2), (4) Date: Jun. 6, 2007

(87) PCT Pub. No.: WO2006/065900
PCT Pub. Date: Jun. 22, 2006

(65) Prior Publication Data
US 2009/0123955 A1    May 14, 2009

Related U.S. Application Data

(60) Provisional application No. 60/635,711, filed on Dec. 13, 2004.

(51) Int. Cl.
*C12Q 1/58* (2006.01)
*C12Q 1/00* (2006.01)
*C12Q 1/62* (2006.01)
*C12Q 1/26* (2006.01)
*G01N 17/04* (2006.01)

(52) U.S. Cl. .................. 435/14; 435/4; 435/10; 435/11; 435/15; 435/25; 435/26; 205/777.5

(58) Field of Classification Search ........................ None
See application file for complete search history.

(56) References Cited

U.S. PATENT DOCUMENTS

| | | | |
|---|---|---|---|
| 3,630,957 A | 12/1971 | Hans-Georg Rey et al. . | 252/408 |
| 3,992,158 A | 11/1976 | Przybylowicz et al. | |
| 3,993,451 A | 11/1976 | Verbeck | |
| 4,211,845 A | 7/1980 | Genshaw et al. | 435/14 |
| 4,250,256 A | 2/1981 | Wielinger et al. | 435/32 |
| 4,312,834 A | 1/1982 | Vogel et al. | 422/56 |
| 4,356,149 A | 10/1982 | Kitajima et al. | |
| 4,438,067 A * | 3/1984 | Siddiqi | 422/56 |
| 4,452,887 A | 6/1984 | Kitajima et al. | |
| 4,806,311 A | 2/1989 | Greenquist | |
| 4,808,529 A | 2/1989 | Doppelfeld et al. | 435/179 |
| 4,824,640 A | 4/1989 | Hildenbrand et al. | 422/56 |
| 5,079,140 A | 1/1992 | Albarella et al. | |
| 5,116,729 A | 5/1992 | Ismail et al. | 435/14 |
| 5,126,275 A | 6/1992 | Hatch et al. | 436/169 |
| 5,141,850 A | 8/1992 | Cole et al. | |
| 5,171,688 A | 12/1992 | Hewett et al. | |
| 5,264,348 A | 11/1993 | Schick et al. | 435/28 |
| 5,290,536 A | 3/1994 | Kocher et al. | 424/7.1 |
| 5,300,637 A | 4/1994 | Hatch et al. | 518/162 |
| 5,306,623 A | 4/1994 | Kiser et al. | 435/14 |
| 5,322,680 A | 6/1994 | Beck et al. | 428/71 |
| 5,360,595 A | 11/1994 | Bell et al. | 422/56 |
| 5,382,523 A | 1/1995 | Hoenes et al. | 435/14 |
| 5,393,493 A | 2/1995 | Makino et al. | |
| 5,620,863 A | 4/1997 | Tomasco et al. | 435/14 |
| 5,736,335 A | 4/1998 | Emmons et al. | |
| 5,789,255 A | 8/1998 | Yu | 536/95 |
| 5,801,061 A | 9/1998 | Stephenson | |
| 5,902,731 A | 5/1999 | Ouyang et al. | 435/26 |
| 5,916,156 A | 6/1999 | Hildenbrand et al. | |
| 5,968,765 A | 10/1999 | Grage et al. | 435/25 |
| 6,187,268 B1 | 2/2001 | Albarella et al. | |
| 6,200,773 B1 | 3/2001 | Ouyang et al. | 435/26 |
| 6,524,864 B2 | 2/2003 | Fernandez Decastro | 436/164 |
| 6,586,199 B2 | 7/2003 | Ouyang et al. | 435/26 |
| 6,764,581 B1 | 7/2004 | Forrow et al. | 204/403.14 |
| 0,156,662 A1 | 7/2008 | Wu | |
| 7,439,033 B2 * | 10/2008 | Marfurt | 435/14 |
| 7,713,474 B2 | 5/2010 | Schulman | |
| 2003/0077702 A1 | 4/2003 | Shah et al. | 435/69.1 |
| 2005/0129572 A1* | 6/2005 | Schulman et al. | 422/56 |
| 2009/0178936 A1 | 7/2009 | Zhu | |

FOREIGN PATENT DOCUMENTS

| | | |
|---|---|---|
| EP | 0162302 | 11/1985 |
| EP | 0226465 | 6/1987 |
| GB | 2085159 | 4/1982 |
| JP | 3081666 | 4/1991 |
| JP | 5018959 | 1/1993 |
| JP | 5026875 | 2/1993 |
| WO | WO 00/42422 | 7/2000 |
| WO | WO 03/060517 | 7/2003 |

OTHER PUBLICATIONS

Written Opinion of the International Searching Authority corresponding to co-pending International Patent Application No. PCT/US2005/045235, European Patent Office, dated May 2, 2006, 4 pages.

International Search Report corresponding to co-pending International Patent Application No. PCT/US2005/045235, European Patent Office, dated May 2, 2006, 4 pages.

* cited by examiner

*Primary Examiner* — Herbert J. Lilling
(74) *Attorney, Agent, or Firm* — Nixon Peabody LLP (57) ABSTRACT

A test strip or electrochemical sensor for measuring the amount of an analyte in a biological fluid, e.g. the glucose content of whole blood, includes a size self-limiting reagent formulation employing an enzyme system for reaction with the analyte, the reactive system mixed into a water-soluble swellable polymer matrix containing small water-insoluble particles having a nominal size of about 0.05 to 20 μm, preferably about 1 to 10 μm. The weight ratio of the water-insoluble particles to the water-soluble swellable polymer matrix is about 1/2 to 2/1. The reagent formulation is deposited onto a non-porous substrate to form a thin layer about 6-16 μm thick, providing a rapid and stable response to application of a sample, while being insensitive to the amount of the sample.

20 Claims, 6 Drawing Sheets

SIZE SELF-LIMITING COMPOSITIONS AND TEST DEVICES FOR MEASURING ANALYTES IN BIOLOGICAL FLUIDS

CROSS-REFERENCE TO RELATED APPLICATIONS

This application claims priority to Application No. 60/635,711 filed on Dec. 13, 2004, which is incorporated by reference in its entirety.

FIELD OF THE INVENTION

This invention relates generally to formulations used in determining the amount of an analyte in biological fluids. In one important application, the invention is applied to measuring the glucose content of blood or other fluids.

BACKGROUND OF THE INVENTION

The quantitative determination of analytes in biological fluids such as whole blood is of great importance in the diagnosing and treating of certain medical conditions. For example, determining the glucose level in the blood of diabetic individuals, who must frequently check the glucose level in their blood to regulate their diets and medication. Measuring the glucose content of blood can be done by several methods. One method employs an electrochemical biosensor that relates glucose content to a measured electrical current. Another method provides a visual indication of the glucose content, such as by developing a color by reaction of an indicator. While the present invention is particularly useful in optical measurements, it also has application to electrochemical biosensors.

There have been many patents describing methods employing indicators that develop color or other measurable responses when they are chemically oxidized as the last step of a series of reactions. For example, methods that employ enzymes, such as, analyte oxidases (e.g. glucose oxidase) or analyte dehydrogenases (e.g. glucose dehydrogenase). The procedures used are similar, but they employ different enzymes, mediators and indicators.

Methods using glucose oxidase enzymes are taught in many US patents and patent applications. Representative are U.S. Pat. Nos. 4,211,845; 4,808,529; 5,116729; 5,264,348; 5,620,863; and 2003/0077702 A1. These patents teach a method in which glucose is oxidized to gluconic acid with the release of hydrogen peroxide. The hydrogen peroxide is said to oxidize an indicator in the presence of a peroxidase to produce a measurable color, indicating the glucose content of the blood sample. Some recent patents suggest a process in which the glucose is converted first to gluconic acid and then to gluconolactone with the release of hydrogen peroxide. It has also been suggested that the gluconolactone is formed first and then hydrolyzed to gluconic acid. Regardless of which process scheme is correct, glucose oxidase enzymes have been used widely in dry strips and in other techniques for measuring the glucose content of blood.

Various indicators have been employed in glucose sensors, such as benzidine-type indicators and heterocyclic azines. For example, 3,3',5,5'-tetramethylbenzidine and syringaldazine, luminol, o-tolidine, o-dianisitine, among others. Another family of indicators is tetrazolium dye precursors. Examples of patents describing such indicators include U.S. Pat. Nos. 5,126,275, 5,322,680, 5,300,637, 5,290,536, 5,360,595 and 6,586,199. Tetrazolium indicators are used in a preferred embodiment of the invention to be described below.

Of particular interest with regard to the present invention is the method described in U.S. Pat. No. 6,200,773 and its parent U.S. Pat. No. 5,902,731. In these patents, a test of the glucose content of blood employs glucose dehydrogenase, as a cofactor NAD or PQQ or their derivatives, a tetrazolium dye precursor, a diaphorase enzyme or an analog, and a nitrite salt. FIG. 5 of the '773 patent is a diagram of the process by which glucose is detected by development of color from the reduction of the tetrazolium dye precursor to formazan.

An early patent relating to the use of enzymes to determine the amount of glucose in blood is U.S. Pat. No. 3,630,957. Glucose oxidise and peroxidase were uniformly distributed in a water-resistant polymer film to react with glucose and to produce a color. The film could be supported on a substrate, e.g. a polymer film. It was suggested that fillers including chalk, titanium dioxide, colloidal silicic acid (used in the examples) and the like could be added and that pigments could be included to make the films opaque. Blood was applied to the reagent-containing film and then wiped off before reading the developed color. The use of opaque fillers to reduce interference with glucose measurements by red blood cells was also discussed in U.S. Pat. No. 5,968,765.

Another patent of interest is U.S. Pat. No. 4,312,834, which describes the use of a water-resistant film including fine insoluble particles, which provide access to the reagents while blocking access of large components. The film could be supported on carriers, such as films, foils, etc. The patentees were concerned with access of certain molecules, stating that the amount of the fine particles (termed "film openers") should be with certain limits. Various types of particles were suggested, such as kieselguhr gel, silica gel, and gypsum, and the like. Titanium dioxide was suggested, both as a film opener and as a way to improve the remission properties of the film. In general, relatively thick films of 200-400 μm were deposited on substrate films in the examples; in some cases multiple layers were applied. As in the '957 patent, excess of the sample, e.g. blood, was wiped off after the reaction had occurred.

Test strips have been described in many patents, since they are widely used for detection of analytes in biological samples. Each test strip application has its unique problems which must be overcome if accurate and consistent results are to be obtained. Testing whole blood requires that the red blood cells not interfere with the color which is developed to indicate the presence of glucose, or with electrochemical measurements. In some instances specific components are included in the test strips so that the red blood cells are filtered from the sample. In other cases the sample is wiped off after a period of time has elapsed so that the developed color can be measured. Another problem encountered when testing whole blood relates to the concentration of red blood cells in the sample. They are commonly measured by their volume in the sample and referred to as the hematocrit value. Since the hematocrit may vary from 20 to 60% in blood samples, the glucose measurement may be affected. Also, movement of the blood plasma carrying glucose to the reagents to develop color (or an electrochemical response), may be retarded or incomplete.

Preventing red blood cells from reaching the reagents that react with glucose has been a concern of many workers in the art. In the test strip of the '765 patent mentioned above, to a 0.002 to 0.2 inch (50.8 to 5080 μm) thick porous membrane was added an agent for separating red blood cells from whole blood, which included polyacrylic acid among others, an indicating reagent and an opaque filler, e.g. titanium dioxide, talc, etc. The coating solution was deposited on the surface of the porous membrane or imbibed within the membrane.

In U.S. Pat. No. 5,306,623 a coating capable of separating whole blood was selected from a group of polymers including polyvinyl sulfonic acid, polyethylene glycol, polystyrene sulfonic acid, hydroxypropyl cellulose, polypropylene glycol, polyvinyl pyrrolidone and polyacrylic acid. The separating coating was deposited on a porous matrix along with reagents for testing blood.

Sensitivity of blood test strips to the hematocrit of whole blood was discussed in U.S. Pat. No. 5,789,255, The inventor found that addition 0.1-2% w/v of a high molecular weight (>750,000) acrylic acid polymer reduced the effect of varying hematocrit on the glucose measurements.

The ideal test strip for measuring glucose in whole blood samples would be insensitive to the hematocrit of the blood sample and provide rapid, accurate, and consistent results. A fast response time combined with a stable endpoint would provide a test that is significantly less time dependent and therefore more convenient in the hands of the user. In another aspect of importance to the user, the test strip should be insensitive to the volume of blood applied. The test strip to be described in more detail below closely approaches that ideal performance.

SUMMARY OF THE INVENTION

The invention generally relates to size self-limiting reagent formulations used in optical or electrochemical methods to measure analytes in biological fluids and test strips containing the reagent formulation. Although glucose is an analyte of particular interest, other analytes in other biological fluids are considered to be within the scope of the present invention.

The inventive formulation in general includes a water-soluble swellable polymer matrix containing water-insoluble particles having a nominal size of about 0.05 to 20 μm, preferably about 1 to 10 μm, and an enzyme system for reacting with an analyte. The weight ratio of water-insoluble particles to the water-soluble swellable polymer matrix is about 1/2 to 2/1.

In one preferred embodiment, the reagent formulation of the invention includes as reactants an enzyme system for reaction with glucose and an indicator. The enzyme system includes glucose dehydrogenase and a co-factor for the enzyme, e.g. NAD, a tetrazolium salt indicator, and the enzyme diaphorase as a mediator in a particularly preferred embodiment. The reagents are combined with a water-soluble swellable polymer matrix containing small water-insoluble particles, preferably titanium dioxide and calcium carbonate. The polymer matrix preferably is chosen from among polyacrylic acid, polyvinyl alcohol, polystyrene sodium sulfuric acid, polyacrylic latexes, polyethyleneglycol, styrene acrylates, and their co-polymers. The weight ratio of the particles to the polymer matrix preferably is about 1/2 to 2/1. In making a test strip, the formulation of the invention is cast as a membrane with a thickness of about 6 to 16 μm, preferably about 7 to 10 μm on a non-porous substrate. The membrane is covered with an adhesive layer including a capillary passageway and a protective top to complete the test strip. The cover may be clear or opaque.

In another aspect, the invention is a method of testing by optical or electrochemical methods for an analyte in a biological fluid, e.g. glucose in whole blood, that provides a rapid and stable response and is insensitive to the amount of the sample. The method of the invention employs a test strip in which a thin membrane is cast on a non-porous substrate, the membrane including water-insoluble particles having a nominal size of 0.05 to 20 μm, preferably 1-10 μm, in a water-soluble swellable polymer matrix. The thin membrane preferably has a thickness of about 6 to 16 μm, more preferably about 7 to 10 μm and the weight ratio of reflective particles to the polymer matrix preferably is about 1/2 to 2/1.

BRIEF DESCRIPTION OF THE DRAWINGS

FIG. 1 *a* is a plot of the results of Example 1.
FIG. 1 *b* is another plot of the results of Example 1.
FIG. 2 *a* is a plot of the results of Example 2.
FIG. 2 *b* is another plot of the results of Example 2.
FIG. 3 *a* is a plot of the results of Example 3.
FIG. 3 *b* is another plot of the results of Example 3.
FIG. 3 *c* is yet another plot of the results of Example 3.
FIG. 4 *a* is a plot of the results of Example 4.
FIG. 4 *b* is another plot of the results of Example 4.
FIG. 4 *c* is yet another plot of the results of Example 4.

DESCRIPTION OF THE PREFERRED EMBODIMENTS

The invention generally relates to formulations for measuring analytes in biological fluids, including but not limited to glucose, lactate, cholesterol, triglycerides, free fatty acids, bilirubin, ascorbate, hydrogen peroxide, and uric acid. One important application of the invention is measuring the glucose content of whole blood, which is described in more detail below. It will be evident to those skilled in the art that the formulations may substitute other reagents for those used to measure glucose.

Measuring Glucose in Blood
Optical Methods

Glucose in blood may be determined by reagent systems that employ enzymes to oxidize glucose, including without limitation hexolinase, glucose-6-phosphate dehydrogenase, glucose dehydrogenase, glucose dehydrogenase-PQQ, and glucose oxidase.

In the methods which employ glucose oxidase, those enzymes react with glucose, producing oxidized glucose and hydrogen peroxide. The hydrogen peroxide oxidizes an indicator compound in the presence of a peroxidase. The oxidized indicator produces a color which is correlated with the glucose content of the blood sample.

In other embodiments of the present invention, a glucose dehydrogenase is used, along with a co-factor, such as NAD, FAD or PQQ, a mediator, e.g. diaphorase, and an indicator, such as tetrazolium dye precursor to produce a visible response proportional to the glucose content of the sample. Such reactions are normally described by the following sequence of reactions:

Glucose+GDH-co-factor$_{oxid}$→Gluconolactone+GDH-co-factor$_{red}$

GDH-co-factor$_{red}$+Mediator$_{oxid}$→GDH-co-factor$_{oxid}$+Mediator$_{red}$

Mediator$_{red}$+tetrazolium indicator→Mediator$_{oxid}$+Formazan

According to this sequence of reactions, glucose is converted to gluconolactone while the dehydrogenase-co-factor is reduced and then reoxidized by a mediator for further reaction with available glucose.

Dehydrogenases

A dehydrogenase specific for reaction with glucose is termed a glucose dehydrogenase. They are commercially available from Toyobo, Kyowa, Amano, Genzyme, Biozyme and others and are either native enzymes or recombinant enzymes produced by classic fermentation and/or recombinant methods. In order to be effective, such dehydrogenases require a co-factor, such as NAD (nicotinamide adenine dinucleotide) and its derivatives, FAD (flavin adenine dinucleotide) and its derivatives, and PQQ (pyrroloquinoline quinone) and its derivatives.

Mediators

A mediator is typically used to reoxidize the reduced dehydrogenase-co-factor after the reaction with glucose to form the corresponding lactone. Examples of mediators (called a hydride extractor in U.S. Pat. No. 6,200,773 include diaphorase, PMS (phenazine methosulfate), PES (phenazine ethosulfate), DCIP (2,6-dichlorophenolindophenol), and ferrocene. A commonly used mediator in electrochemical sensors is ferricyanide.

Tetrazolium Indicators

Tetrazolium indicators are generally described in U.S. Pat. No. 5,360,595 and others mentioned above. In U.S. Pat. No. 6,200,773 certain tetrazolium dye precursors are listed as being particularly useful in reactions with dehydrogenase-co-factor combinations. Among them is the tetrazolium compound designated WST-4, used in the examples below.

Supportive Substrates

The reagent layer of the invention typically is placed on a substantially non-porous supporting substrate, typically a polymer strip or handle such as a polyester, polycarbonate or the like. Such strips will have dimensions suited for use with the instrument used to read the developed color. For example, the strips described in the examples will be about 0.060 by 0.160 inches (1.5 by 4.1 mm) and have a thickness of about 0.002 in (51 μm). Although not critical to the invention, the substrates preferably will be optically clear and may contain one or more coatings applied during their manufacture to help with adhesion to other surfaces, such as the reagent-carrying layer.

Electrochemical Methods

In electrochemical sensors a potential is applied to electrodes in contact with a blood (or other) sample to produce an electrical current that is measured and correlated with the amount of the analyte (e.g. glucose) in the sample. The electrodes are in contact with a solid layer containing enzyme reagents that oxidize the analyte in the sample and mediators that reoxidize the reduced enzyme. The reactors may be described by the following steps:

$$Glucose + E_{oxid} \rightarrow E_{red} + \text{Oxidized Glucose (Gluconolactone)}$$

$$E_{red} + n\text{Med}_{oxid} \rightarrow n\text{Med}_{red} + E_{oxid}$$

$$n\text{Med}_{oxid} \rightarrow \text{Med}_{oxid} + ne^-$$

Where $E_{oxid}$ and $E_{red}$ are oxidized and reduced forms of the redox center of the enzyme and $\text{Med}_{oxid}$ and $\text{Med}_{red}$ are oxidized and reduced forms of the mediator.

In general, the reactive formulation used in electrochemical sensors will be similar to that used in optical methods, except that the indicators are not required.

Reagent Layer Formulations

The reagent layer of the invention is a single very thin layer containing reagents which react with glucose in a blood sample and produce a quick and uniform response. The reagent layer may be characterized as being size self-limiting in that it blocks movement of large particles, such as red blood cells, and permits movement of desired components. It may be described generally as a water-soluble swellable polymer matrix containing water-insoluble particles, and an enzyme for reaction with glucose, such as a glucose dehydrogenase and its co-factor, a mediator and an indicator where optical detection is used. Additional components may include detergents, surfactants, and the like.

The polymers may include polyacrylic acid, polyvinyl alcohol, polystyrene sodium sulfonic acid, polyacrylic latex, polyethylene glycol, styrene acrylates and their co-polymers. Generally such polymers are characterized by having relatively low molecular weight, for example 100 to 100,000 daltons, including low molecular weight oligomers. Such polymers will have high solubility in aqueous solutions and typically have low viscosity. They typically will be dissolved in a buffered solution to maintain a desired pH, e.g. about 7.5. The polymers will rapidly swell when rehydrated in neutral pH solutions such as whole blood. It is believed that such polymers provide the rapid access of the analyte (e.g. glucose) to the reagents.

Particles may include titanium dioxide, calcium carbonate, bentonite clay, silica, barium sulfate, powdered metals, latex and the like. Suitable particles are essentially insoluble in water and have a nominal size of about 0.05 to 20 μm, but preferably are in the 1 to 10 μm range. The particles should not have pores that permit undesirable migration of reagents or sample components.

Detergents and surfactants may include proprietary materials, such as Silwet L-7600 (Polydimethylsiloxane methyl-ethoxylate), Gerepon T-77, (Sodium N-oleyl-N-methyltaurate), and Zwittergentt 3-12 (N-Dodecyl-N,N-dimethyl-3-ammonio-1-propanesulfonate), among others.

Other additives which may be included are emulsifiers, wetting agents, thickeners, pigments, and similar additives.

After the coating has been applied and dried, the weight ratio of the reflective particles to the polymer matrix is typically between about 1/2 to 2/1. As applied, the coating may be from 6 to 16 μm thick, preferably about 7 to 10 μm. Such coatings are much thinner than those commonly used in the art. It was surprising to find that such thin layers could provide rapid and stable response, as will be illustrated in the examples below.

Preparing a Test Strip for Optical Methods

The reagent layer is prepared by blending the components described above into a uniform aqueous coating, which is applied to a substrate using techniques familiar to those skilled in the art, such as gravure or Mayer-rod coating, and dried. Other coating methods may be used, since the method of applying the coating is not considered essential to success.

After applying the coating to the substrate, it will be covered with a protective top, preferably a hydrophilic-coated polyester, which may be transparent or opaque. An additional opaque layer may also be added. Between the reactive layer and the protective top is placed an adhesive layer that joins the other two layers and also forms a capillary passageway for introducing blood samples. As will be seen in the examples, the test strips of the invention are not sensitive to the dimensions of the capillary. That is, the test strips do not require that a fixed amount of blood (or other biological fluid) be applied.

In each of the examples below, the components listed were combined by blending polymers, buffers, particles, and adjuvants into distilled water, first at low and then high sheer, for a period of time until uniformly mixed to make the base material. Then, the diagnostic reagents were blended into the base material and the blended components were applied to strips of a substantially non-porous polycarbonate or polyester support material as a 10 μm thick coating. A spacer-adhesive layer of 3M F9460 was added, having a thickness of 50 or 80 μm. Finally a protective top of a hydrophilic-coated polyester (3M 9971) was applied by use of transfer adhesive. A piece of opaque material was applied to the outside of the polyester top to provide a small amount of added opaqueness.

Electrochemical Sensors

The reagent layer, excluding the optical indicator, will be applied to electrodes to produce an electrochemical sensor, such as those described for example in U.S. Published Application 2001/0042683.

Example 1

Figure 1A:
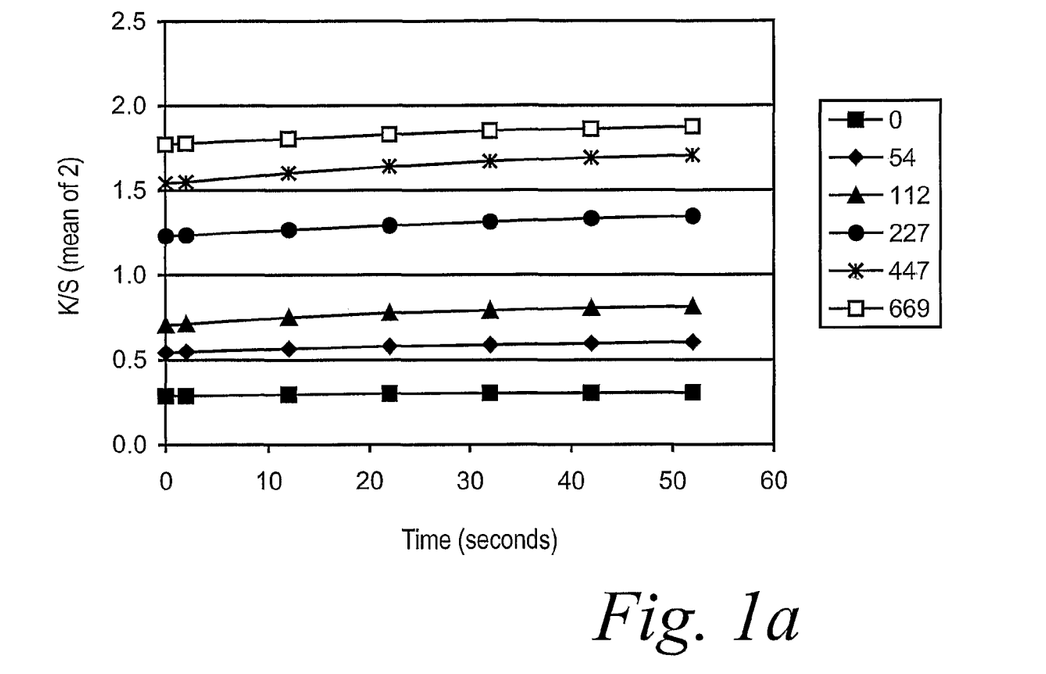
Figure 1B:
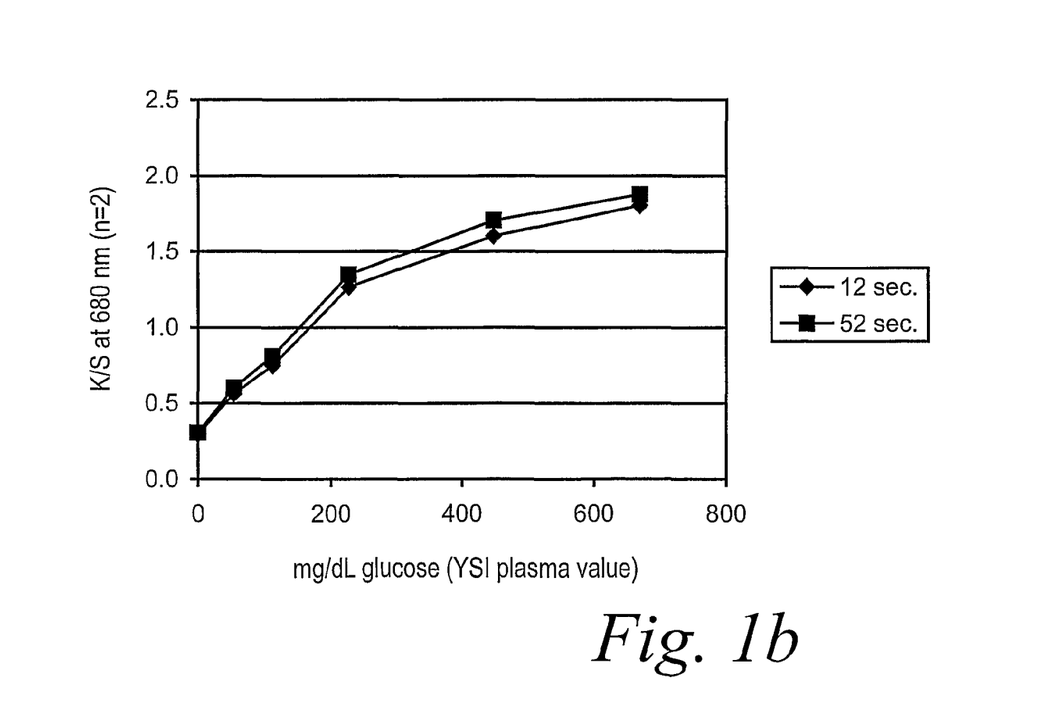

A reagent layer was prepared by blending the components listed in Table A, applying them to a substrate, and completing the test strip as described above. The performance of the test strips was measured by adding a small sample of whole blood (about 600 nL) containing a known amount of glucose to the reagent layer, placing the strip in a small read area (e.g. 0.75 mm diameter) diffuse reflectance measuring instrument and reading the color developed over a period of about 60 seconds. The results are reported as K/S, the Kubelka-Munk function $(1-R)^2/2R$ where R is the measured reflectance. As will be seen in FIG. 1a the measured color intensity remained constant over the period for each of the glucose concentrations tested. The response of the glucose meter was plotted versus the glucose content, as shown in FIG. 1b. It will be clear that the response time was rapid and that the results for 12 second and 52 seconds were very similar. Thus, one can conclude that the test strips of the invention provide a rapid response and are not unduly sensitive to the time of reading.

TABLE A

| Component | Concentration |
| --- | --- |
| Potassium Phosphate, pH 7.5 | 120 mm |
| Bentonite clay[1] | 0.78% |
| Titanium dioxide[2] | 5% $TiO_2$ |
| Polyacrylic acid, sodium salt (60k)[3] | 1.0% |
| Gerepon T-77[4] | 0.45% |
| Silwet L-7600[5] | 0.10% |
| PEG 8000[6] | 2.0% |
| WST-4 tetrazolium salt[7] | 40 mM |
| NAD[8] | 10 mM |
| Diaphorase[9] | 1900 µ/mL |
| Glucose dehydrogenase[10] | 1100 µ/mL |

[1]Rheox, Bentone EW
[2]Sigma-Aldrich, T-8141
[3]Polysciences, Inc., 18611
[4]Pragmatics, Inc.
[5]OSi Specialties
[6]Pragmatics, Inc.
[7]Dojindo Laboratories
[8]Calbiochem
[9]Unitika, Diaphorase I
[10]Amano Enzyme Inc., Amano 2

Example 2

Figure 2A:
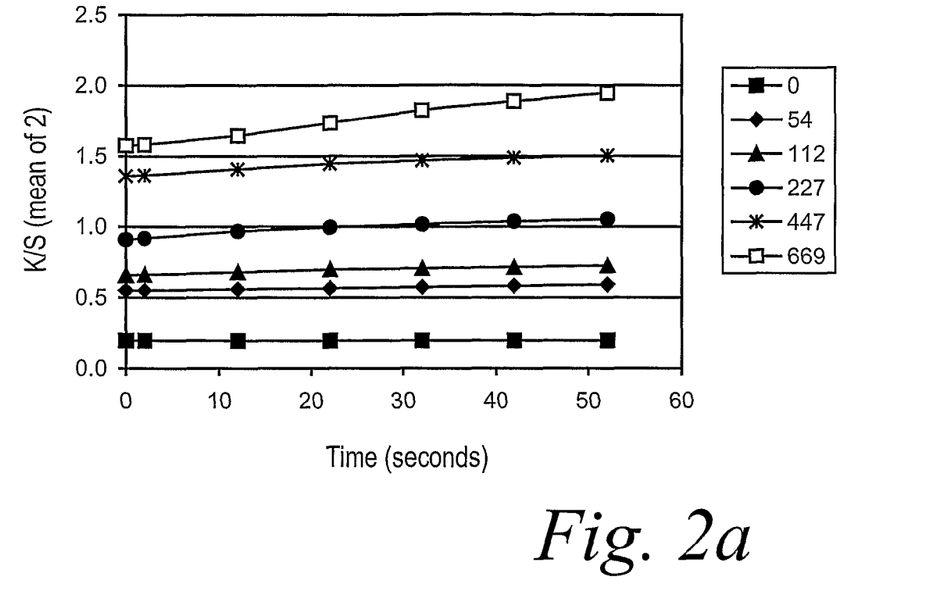
Figure 2B:
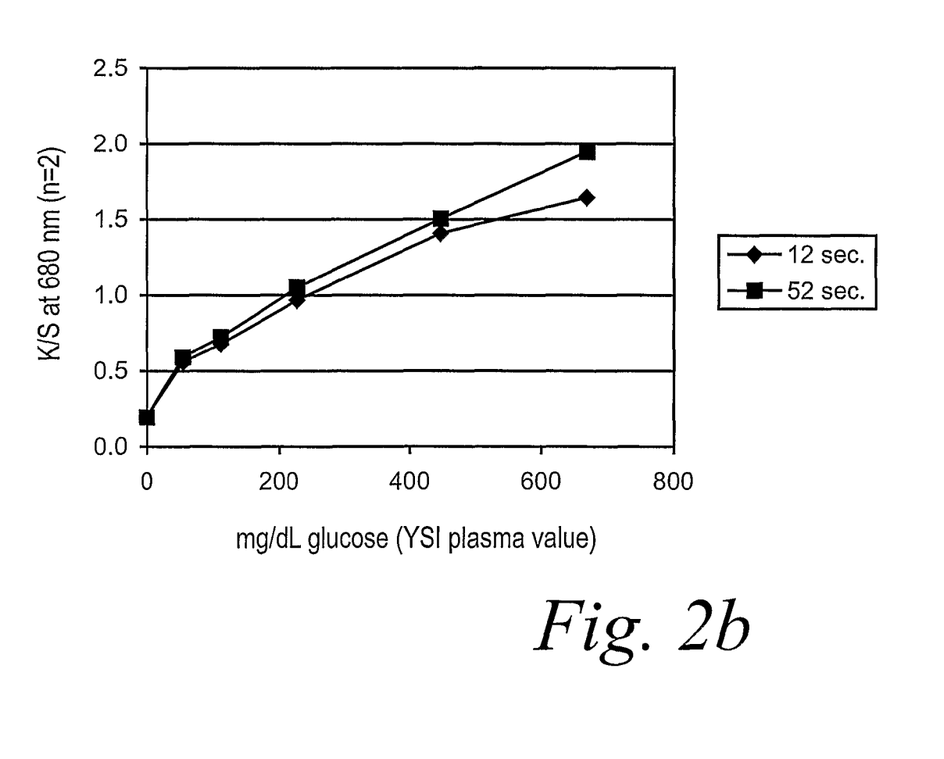

Another reagent layer was prepared by blending the components listed in Table B, applying them to a substrate and completing the test strip as described above. A series of tests were carried out as in Example 1 with whole blood samples containing known amounts of glucose. The results of the tests are shown in FIGS. 2a-b. It will be seen that the color developed was substantially constant over a 60 second period of time, except that some additional color was developed at higher concentrations.

TABLE B

| Component | Concentration |
| --- | --- |
| Potassium phosphate, pH 7.5 | 120 mm |
| Bentonite clay[1] | 0.78% |
| Titanium dioxide[2] | 5.3% $TiO_2$ |
| PSSA (70k)[3] | 1.8% |
| Acrylic Latex[4] | 3.6% |
| Zwittergent 3-12[5] | 0.2% |
| WST-4 tetrazolium salt[6] | 40 mm |
| NAD[7] | 10 mm |
| Diaphorase[8] | 1900 µ/mL |
| Glucose dehydrogenase[9] | 1100 µ/mL |

[1]Rheox, Bentone EW
[2]Sigma-Aldrich, T-8141
[3]Polysciences, Inc.
[4]Dow, UCAR Latex 455
[5]Calbiochem
[6]Dojindo Laboratories
[7]Sigma-Aldrich
[8]Unitika, Diaphorase I
[9]Amano Enzyme Inc., Amano 2

Example 3

Figure 3A:
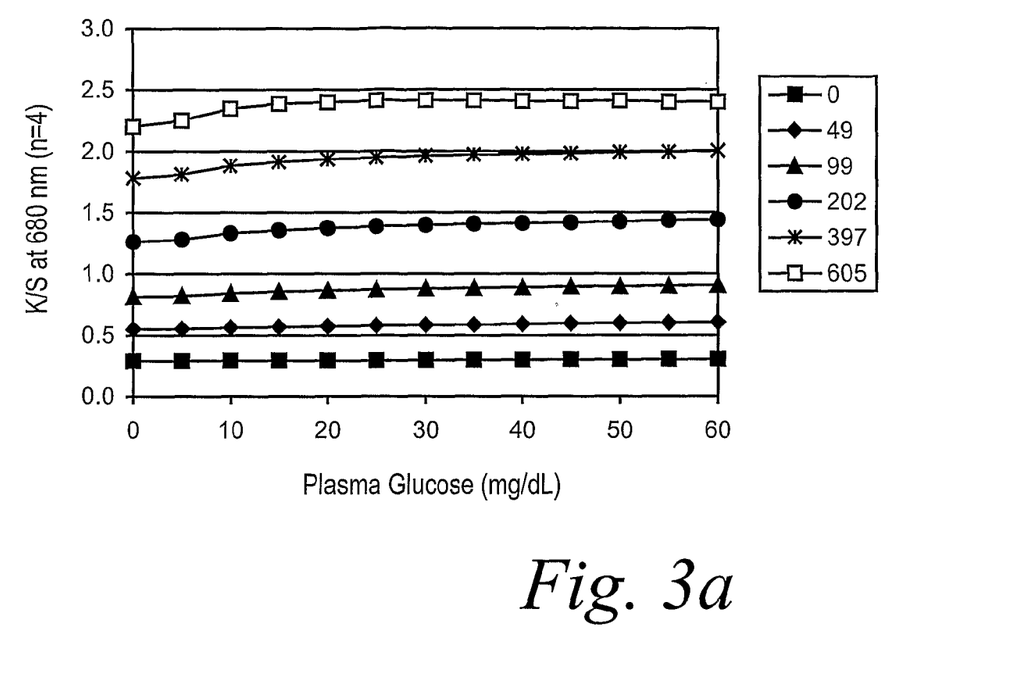
Figure 3B:
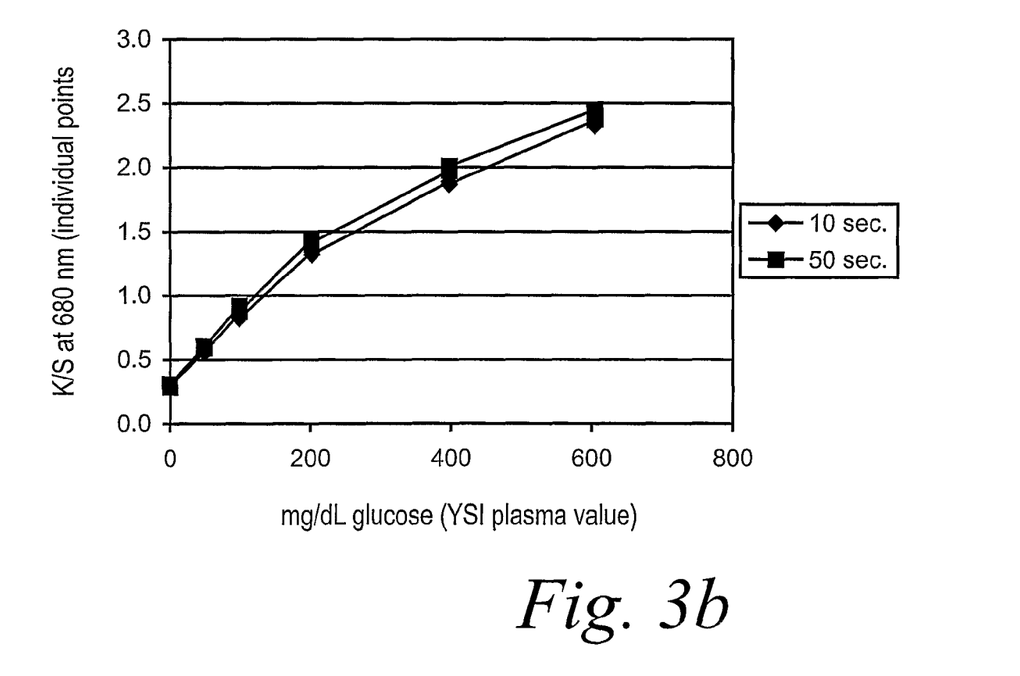

A reagent layer was prepared by blending the components listed in Table C, applying them to a substrate, and completing the test strip as described above. The reagent layer was tested as in Examples 1 and 2. The results are shown in FIG. 3a, b, c. FIGS. 3a and 3b report results similar to those of Examples 1 and 2. The additional color development at higher glucose concentrations noted in FIGS. 2a and b does not appear in this example.

Figure 3C:
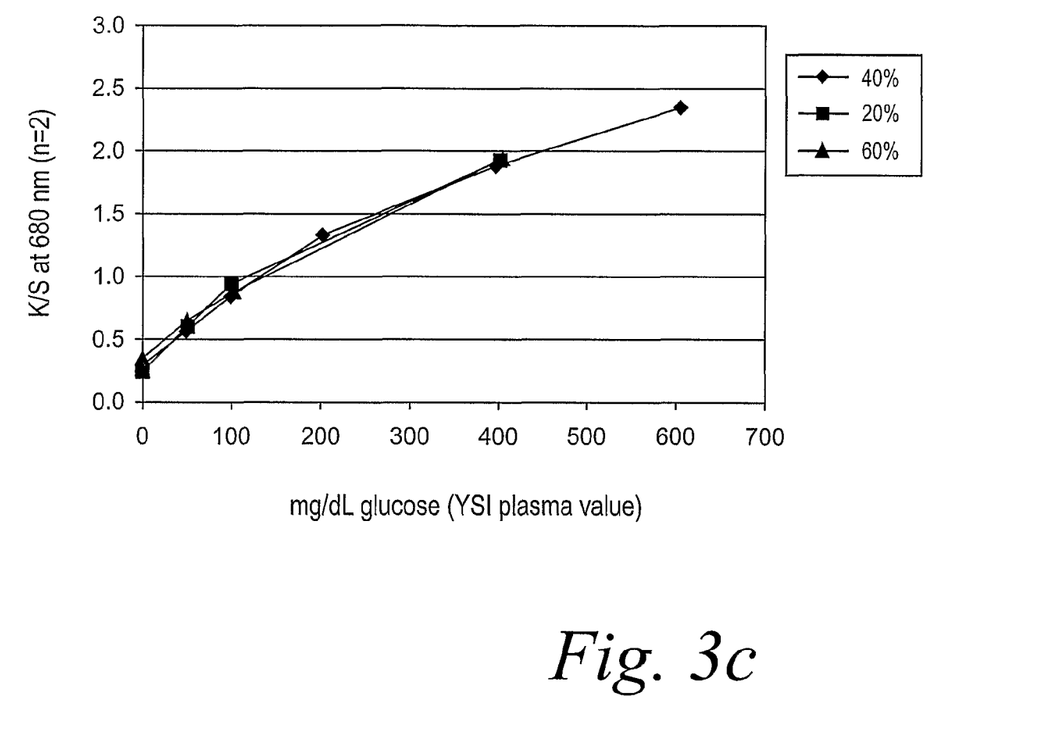

Additional results are shown in FIG. 3c. Samples of whole blood having three distinct hematocrits (20%, 40%, 60%) were measured and the results plotted. It will be clear that the test strip of the invention is not affected significantly by the concentration of red blood cells in the blood.

TABLE C

| Components | Concentration |
| --- | --- |
| Hepes, half sodium salt[1] | 0.3 m |
| Bentonite clay[2] | 1.44% |
| Titanium dioxide[3] | 8% $TiO_2$ |
| Polyacrylic acid, sodium salt (60k)[4] | 3.85% |
| PEG 8000[5] | 2.0% |
| Rhodasurf-ON870[6] | 1.0% |
| Gerepon T-77[7] | 0.6% |
| Silwet L-7600[8] | 0.08% |
| WST-4 tetrazolium salt[9] | 60 mm |
| NAD[10] | 10 mm |
| Diaphorase[11] | 1085 µ/ml |
| Glucose dehydrogenase[12] | 2680 µ/ml |

[1]Research Organics
[2]Rheox, Bentone EW
[3]Sigma-Aldrich, T-8141
[4]Polysciences, Inc.
[5]Pragmatics, Inc.
[6]Pragmatics, Inc.
[7]Pragmatics, Inc.
[8]OSi Specialties
[9]Dojindo Laboratories
[10]Sigma-Aldrich, #N-6522
[11]Unitika, Diaphorase I
[12]Toyobo Co., Ltd., #GLD311

Example 4

Figure 4A:
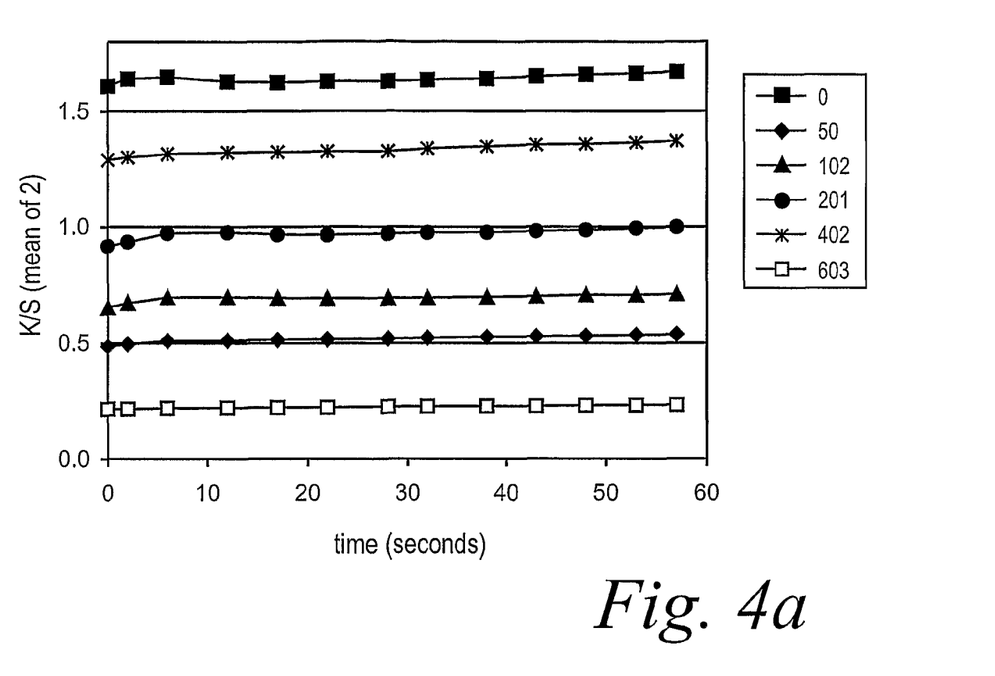
Figure 4B:
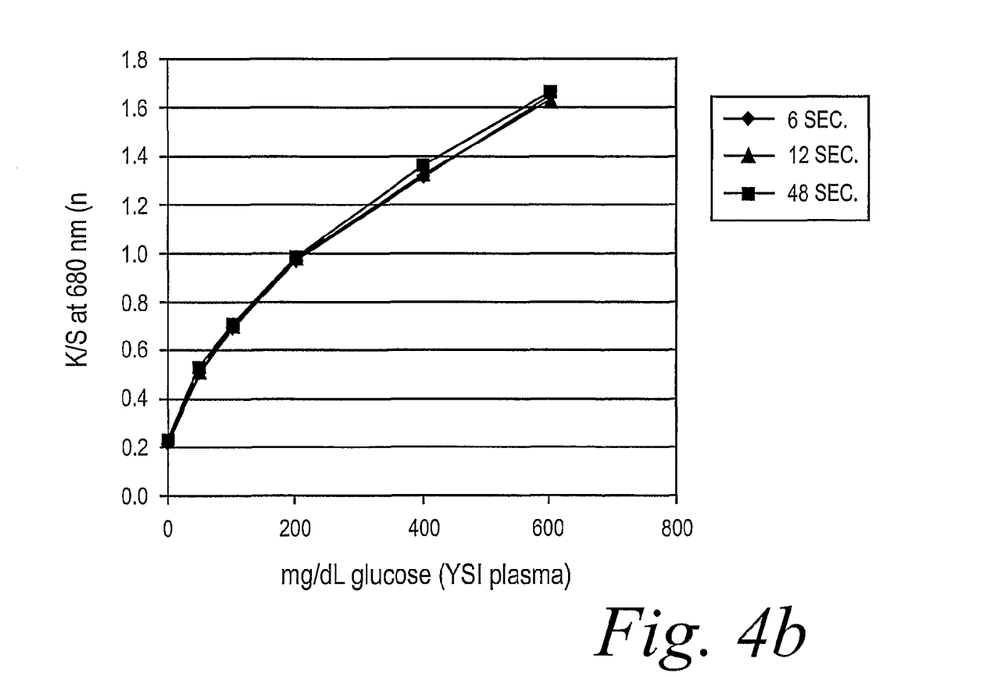
Figure 4C:
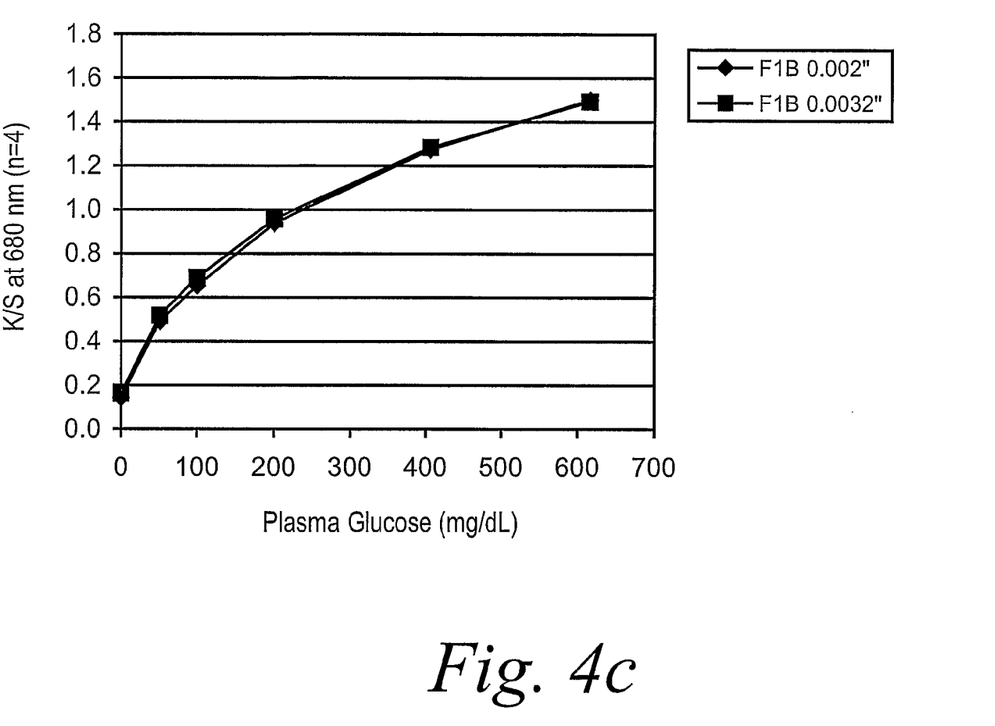

A reagent layer was prepared by blending the components listed in Table D, applying them to a substrate, and completing the test strip as described above. The resulting test strip was tested as in the previous examples. The results are shown in FIG. 4a,b,c. The consistency of measured color development is even greater than found with previous examples. That is, one can conclude that color development is substantially complete within the first few seconds.

FIG. 4c shows another advantage of test strips of the invention. Two test strips designs were compared. The first had a 50 μm capillary gap through which the blood sample entered, while the second type had an 80 μm capillary gap. FIG. 4c shows that this difference in capillary gap height and the resulting change in sample volume has no significant effect on the results. The reason for this result is not clear, but it may be due to an inability of glucose to diffuse from the blood sample into the reagent layer after it has been initially rehydrated by the blood sample. In any event, this represents a significant advantage for the test strips of the invention since it means that they are not sensitive to the quantity of blood applied.

TABLE D

| Component | Composition |
|---|---|
| Sodium phosphate, pH 7.4 | 0.25 mm |
| Polyacrylic acid (60k)[1] | 6% |
| Polyvinyl alcohol (6k)[2] | 6% |
| TiO2[3] | 15% |
| CaCO3[4] | 10% |
| Gerepon T-77[5] | 0.6% |
| Surfonyl DF37[6] | 0.5% |
| Silwet L-7600[7] | 0.1% |
| WST-4 tetrazolium salt[8] | 100 mM |
| NAD[9] | 19 mM |
| Diaphorase[10] | 1800 μ/mL |
| Glucose dehydrogenase[11] | 4020 μ/mL |

[1]Polysciences, Inc.
[2]Polysciences, Inc.
[3]DuPont, R-706
[4]Huber Inc., Optifil☐
[5]Pragmatics, Inc.
[6]Air Products and Chemicals, Inc.
[7]OSi Specialties
[8]Dojindo Laboratories
[9]Sigma-Aldrich, #N-6522
[10]Unitika, Diaphorase I
[11]Toyobo Co., Ltd., #GLD311

Alternate Embodiment A

A reactive formulation for measuring the amount of an analyte in a biological fluid comprising:
(a) a water-soluble swellable polymer matrix;
(b) water-insoluble particles having a nominal size of about 0.05 to 20 μm;
(c) an enzyme system for reacting with said analyte; and
wherein the weight ratio of said water-insoluble particles to said water-soluble swellable polymer matrix is about 1/2 to 2/1.

Alternate Embodiment B

A reactive formulation of Alternate Embodiment A wherein said enzyme system is formulated to reactive with a member of the group consisting of glucose, lactate, cholesterol, triglycerides, free fatty acids, bilirubin, ascorbate, hydrogen peroxide and uric acid.

Alternate Embodiment C

A reactive formulation of Alternate Embodiment A wherein said analyte is glucose and the enzyme system includes a member of the group consisting of hexokinase, glucose-6-phosphate dehydrogenase, glucose dehydrogenase, glucose dehydrogenase-PQQ, and glucose oxidase.

Alternate Embodiment D

A reactive formulation of Alternate Embodiment A wherein said particles are at least one member of the group consisting of titanium dioxide, calcium carbonate, silica, barium sulfate, powdered metals, and latex.

Alternate Embodiment E

A reactive formulation of Alternate Embodiment A wherein said water-soluble swellable polymer matrix includes at least one member of the group consisting of polyacrylic acid, polyvinyl alcohol, polystyrene sodium sulfonic acid, polyacrylic latex, polyethylene glycol, styrene acrylates, and their co-polymers.

Alternate Embodiment F

A reactive formulation of Alternate Embodiment A further comprising at least one surfactant, detergent, or thickener.

Alternate Embodiment G

A reactive formulation of Alternate Embodiment A applied as a coating having a thickness of about 6 to 16 μm.

Alternate Embodiment H

A reactive formulation of Alternate Embodiment G wherein said coating has a thickness of 7 to 10 μm.

Alternate Embodiment I

A reactive formulation of Alternate Embodiment A wherein said water-soluble swellable polymer has a molecular weight below about 100,000.

Alternate Embodiment J

A reactive formulation of Alternate Embodiment A wherein said water-insoluble particles have a nominal size of about 1 to 10 μm.

Alternate Process K

A method of measuring the amount of an analyte in a biological fluid by applying a sample of said biological fluid to a test strip or electrochemical sensor and obtaining a rapid and stable response that is not sensitive to the volume of said sample, said method comprising:
(a) applying a sample of said biological fluid to said test strip or electrochemical sensor, said test strip or electrochemical sensor comprising a non-porous substrate on which is deposited a thin film containing an enzyme system for reacting with said analyte in a formulation including a water-soluble swellable polymer matrix, and water-insoluble particles having a nominal size of about 0.05 to 20 μm; and
(b) measuring the response of said sample to said enzyme system by optical or electrochemical methods and determining the amount of said analyte present in said biological fluid.

Alternate Process L

A method of Alternate Process K wherein said analyte is glucose and said biological fluid is whole blood.

Alternate Process M

A method of Alternate Process L wherein said enzyme system includes a glucose oxidase or a glucose dehydrogenase.

Alternate Process N

A method of Alternate Process K wherein said thin film has a thickness of about 6 to 16 μm.

Alternate Process O

A method of Alternate Process N wherein said thin film has a thickness of about 7 to 10 μm.

Alternate Process P

A method of Alternate Process K wherein the weight ratio of said particles to said polymer matrix is about 1/2 to 2/1.

Alternate Process Q

A method of Alternate Process K wherein said water-soluble swellable polymer matrix is a polymer matrix that includes at least one member of the group consisting of polyacrylic acid, polyvinyl alcohol, polystyrene sodium sulfuric acid, polyacrylic latex, polyethylene glycol, styrene acrylates and their co-polymers.

Alternate Process R

A method of Alternate Process K wherein said particles are particles that include at least one member of the group consisting of titanium dioxide, calcium carbonate, silica, barium sulfate, powdered metals, and latex.

Alternate Process S

A method of Alternate Process K wherein said swellable polymer has a molecular weight below about 100,000.

Alternate Process T

A method of Alternate Process K wherein said insoluble particles have a nominal size of about 1 to 10 μm.

Alternate Embodiment U

A reactive formulation for measuring the glucose content of whole blood comprising
  (a) a water-soluble swellable polymer matrix;
  (b) water-insoluble particles having a nominal size of about 0.05 to 20 μm;
  (c) an enzyme system for oxidizing said glucose;
  (d) an indicator;
wherein the weight ratio of the reflective particles of (b) to the polymer matrix is about 1/2 to 2/1.

Alternate Embodiment V

A reactive formulation of Alternate Embodiment U wherein said enzyme system includes a member of the group consisting of hexokinase; glucose-6-phosphate dehydrogenase, glucose dehydrogenase, glucose dehydrogenase-PQQ, and glucose oxidase.

Alternate Embodiment W

A reactive formulation of Alternate Embodiment U wherein said enzyme system comprises glucose dehydrogenase, a co-factor for said glucose dehydrogenase, a tetrazolium salt indicator, and a mediator.

Alternate Embodiment X

A reactive formulation of Alternate Embodiment U wherein said particles are at least one member of the group consisting of titanium dioxide, calcium carbonate, silica, barium sulfate, powdered metals, and latex.

Alternate Embodiment Y

A reactive formulation of Alternate Embodiment U wherein said water-soluble swellable polymer matrix includes at least one member of the group consisting of polyacrylic acid, polyvinyl alcohol, polystyrene sodium sulfuric acid, polyacrylic latex, polyethylene glycol, styrene acrylates, and co-polymers thereof.

Alternate Embodiment Z

A reactive formulation of Alternate Embodiment U wherein said water-soluble swellable polymer is dissolved in a solution buffered to maintain a desired pH.

Alternate Embodiment AA

A reactive formulation of Alternate Embodiment U further comprising at least one surfactant, detergent, or thickener.

Alternate Embodiment BB

A reactive formulation of Alternate Embodiment U applied as a coating having a thickness of about 6 to 16 μm.

Alternate Embodiment CC

A reactive formulation of Alternate Embodiment BB wherein said coating has a thickness of 7 to 10 μm.

Alternate Embodiment DD

A reactive formulation of Alternate Embodiment U wherein said water-soluble swellable polymer has a molecular weight below about 100,000.

Alternate Embodiment EE

A reactive formulation of Alternate Embodiment U wherein said insoluble particles have a nominal size of about 1 to 10 μm.

Alternate Embodiment FF

A test strip for measuring the glucose content of whole blood samples comprising:
  (a) a substantially non-porous substrate;
  (b) a reagent layer disposed on said substrate, said reagent layer comprising;
    (1) a water-soluble swellable polymer matrix;
    (2) water-insoluble particles having a nominal size of about 0.05 to 20 μm;
    (3) an enzyme system for oxidizing said glucose, and;
    (4) an indicator;
  (c) a protective covering for said reagent layer of (b).

(d) an adhesive layer between said reagent layer and said protective covering, said adhesive layer having a capillary channel for receiving said blood sample.

Alternate Embodiment GG

A test strip of Alternate Embodiment FF wherein said enzyme system includes a member of the group consisting of hexokinase, glucose-6-phosphate dehydrogenase, glucose dehydrogenase, glucose dehydrogenase-PQQ, and glucose oxidase.

Alternate Embodiment HH

A test strip of Alternate Embodiment FF wherein said enzyme system comprises glucose dehydrogenase, a co-factor for said glucose dehydrogenase, a tetrazolium salt indicator, and a mediator.

Alternate Embodiment II

A test strip of Alternate Embodiment FF wherein said water-soluble swellable polymer matrix is at least one member of the group consisting of polyacrylic acid, polyvinyl alcohol, polystyrene sodium sulfonic acid, polyacrylic latex, polyethylene glycol, styrene acrylates, and co-polymers thereof.

Alternate Embodiment JJ

A test strip of Alternate Embodiment FF wherein said water-insoluble particles are at least one member of the group consisting of titanium dioxide, calcium carbonate, silica, barium sulfate, powdered metals, and latex.

Alternate Embodiment KK

A test strip of Alternate Embodiment FF wherein the weight ratio of the reflective particles of b(2) to the polymer matrix of (b)(1) is about 1/2 to 2/1.

Alternate Embodiment LL

A test strip of Alternate Embodiment FF wherein said polymer is dissolved in a solution buffered to maintain a desired pH.

Alternate Embodiment MM

A test strip of Alternate Embodiment FF wherein said reagent layer of (b) farther comprises at least one surfactant, detergent, or thickener.

Alternate Embodiment NN

A test strip of Alternate Embodiment MM wherein said reagent layer has a thickness of 6 to 16 μm.

Alternate Embodiment OO

A test strip of Alternate Embodiment NN wherein said reagent layer has a thickness of 7 to 10 μm.

Alternate Embodiment PP

A test strip of Alternate Embodiment FF wherein said swellable polymer has a molecular weight below about 100,000.

Alternate Embodiment QQ

A test strip of Alternate Embodiment FF wherein said particles have a nominal size of about 1 to 10 μm.

Alternate Process RR

A method of measuring the amount of glucose in a sample of whole blood by applying the blood sample to a test strip and obtaining a rapid and stable response that is not sensitive to the volume of the blood sample, said method comprising:
(a) applying said blood sample to said test strip, said test strip comprising a non-porous substrate on which is deposited a thin film containing an enzyme system for reacting with said glucose in a formulation including a water-soluble swellable polymer matrix, water-insoluble particles having a nominal size of about 0.05 to 20 μm, and an indicator; and
(b) measuring the response of said indicator and determining the amount of said glucose in said blood sample.

Alternate Process SS

A method of Alternate Process RR wherein said enzyme system includes a glucose oxidase or a glucose dehydrogenase.

Alternate Process TT

A method of Alternate Process RR wherein said thin film has a thickness of about 6 to 16 μm.

Alternate Process UU

A method of Alternate Process TT wherein said thin film has a thickness of about 7 to 10 μm.

Alternate Process VV

A method of Alternate Process TT wherein the weight ratio of said particles to said matrix is about 1/2 to 2/1.

Alternate Process WW

A method of Alternate Process RR wherein the particles have a nominal size of about 1 to 10 μm.

Alternate Process XX

A method of Alternate Process RR wherein said water-soluble swellable polymer matrix includes at least one member of the group consisting of polyacrylic acid, polyvinyl alcohol, polystyrene sodium sulfuric acid, polyacrylic latex, polyethylene glycol, styrene acrylates, and co-polymers thereof.

Alternate Process YY

A method of Alternate Process RR wherein said particles are at least one member of the group consisting of titanium dioxide, calcium carbonate, silica, barium sulfate, powdered metals, and latex.

Alternate Process ZZ

A method of Alternate Process RR wherein said water-soluble swellable polymer has a molecular weight below about 100,000.

The invention claimed is:

1. A method of measuring the amount of an analyte in a biological fluid, said method comprising:
   (a) applying a sample of said biological fluid to a test strip, said test strip comprising a non-porous substrate on which is deposited a single film comprising an enzyme system for reacting with said analyte in a formulation including a water-soluble swellable polymer matrix, and water-insoluble particles having a nominal size of about 0.05 to 20 μm;
   (b) measuring the response of said sample to said enzyme system by optical or electrochemical methods; and
   (c) determining the amount or concentration of said analyte present in said biological fluid.

2. The method of claim 1, wherein said analyte is glucose and said biological fluid is whole blood.

3. The method of claim 1, wherein said film has a thickness of about 6 to 16 μm.

4. The method of claim 1, wherein the weight ratio of said particles to said polymer matrix is about 1/2 to 2/1.

5. The method of claim 1, wherein said water-soluble swellable polymer matrix is a polymer matrix that includes at least one member of the group consisting of polyacrylic acid, polyvinyl alcohol, polystyrene sodium sulfuric acid, polyacrylic latex, polyethylene glycol, styrene acrylates and their co-polymers.

6. The method of claim 1, wherein said particles include at least one member of the group consisting of titanium dioxide, calcium carbonate, silica, barium sulfate, powdered metals, and latex.

7. The method of claim 1, wherein said analyte is glucose and the enzyme system includes a member of the group consisting of hexokinase, glucose-6-phosphate dehydrogenase, glucose dehydrogenase, glucose dehydrogenase-PQQ, and glucose oxidase.

8. The method of claim 1, wherein the film further comprises at least one surfactant, detergent, or thickener.

9. The method of claim 1, wherein said water-soluble swellable polymer has a molecular weight below about 100,000.

10. The method of claim 1, wherein said water-insoluble particles have a nominal size of about 1 μm to about 10 μm.

11. The method of claim 1, wherein the response of said sample is substantially independent of test time.

12. A method of measuring the amount of glucose in a blood sample, said method comprising:
   (a) applying said blood sample to said test strip, said test strip comprising a non-porous substrate on which is deposited a film comprising an enzyme system for reacting with said glucose in a formulation including a water-soluble swellable polymer matrix, water-insoluble particles having a nominal size of about 0.05 to 20 μm, and an indicator, the film having a thickness of about 6 to 16 μm;
   (b) measuring the response of said indicator; and
   (c) determining the amount or concentration of said glucose in said blood sample.

13. The method of claim 12, wherein the weight ratio of said particles to said polymer matrix is about 1/2 to 2/1.

14. A method of claim 12, wherein said water-soluble swellable polymer matrix is a polymer matrix that includes at least one member of the group consisting of polyacrylic acid, polyvinyl alcohol, polystyrene sodium sulfuric acid, polyacrylic latex, polyethylene glycol, styrene acrylates and their co-polymers.

15. A method of claim 12, wherein said particles include at least one member of the group consisting of titanium dioxide, calcium carbonate, silica, barium sulfate, powdered metals, and latex.

16. The method of claim 12, wherein the enzyme system includes a member of the group consisting of hexokinase, glucose-6-phosphate dehydrogenase, glucose dehydrogenase, glucose dehydrogenase-PQQ, and glucose oxidase.

17. The method of claim 12, wherein the film further comprises at least one surfactant, detergent, or thickener.

18. The method of claim 12, wherein said water-soluble swellable polymer has a molecular weight below about 100,000.

19. The method of claim 12, wherein said water-insoluble particles have a nominal size of about 1 μm to about 10 μm.

20. The method of claim 12, wherein the response of said indicator is substantially independent of test time.

* * * * *

UNITED STATES PATENT AND TRADEMARK OFFICE
CERTIFICATE OF CORRECTION

| | | |
|---|---|---|
| PATENT NO. | : 7,964,372 B2 | Page 1 of 1 |
| APPLICATION NO. | : 11/792456 | |
| DATED | : June 21, 2011 | |
| INVENTOR(S) | : Karen L. Marfurt | |

It is certified that error appears in the above-identified patent and that said Letters Patent is hereby corrected as shown below:

On the Title page, item (56) References Cited, delete "0,156,662 A1" and replace with --2008/0156662 A1--

Signed and Sealed this
Twentieth Day of September, 2011

David J. Kappos
*Director of the United States Patent and Trademark Office*